(12) United States Patent
Gupta et al.

(10) Patent No.: US 10,617,646 B2
(45) Date of Patent: Apr. 14, 2020

(54) PROCESS FOR MANUFACTURING DRY POWDER BLENDS

(71) Applicant: LUPIN ATLANTIS HOLDINGS SA, Zug (CH)

(72) Inventors: Abhishek Gupta, Pembroke Pines, FL (US); Herbert Clark Chiou, Davie, FL (US); Samiran De, Weston, FL (US); Franciscus Koppenhagen, Deerfield Beach, FL (US); Xian-Ming Zeng, Weston, FL (US)

(73) Assignee: LUPIN ATLANTIS HOLDINGS SA, Zug (CH)

( * ) Notice: Subject to any disclaimer, the term of this patent is extended or adjusted under 35 U.S.C. 154(b) by 11 days.

(21) Appl. No.: 15/563,281

(22) PCT Filed: Apr. 1, 2016

(86) PCT No.: PCT/IB2016/000418
§ 371 (c)(1),
(2) Date: Sep. 29, 2017

(87) PCT Pub. No.: WO2016/156970
PCT Pub. Date: Oct. 6, 2016

(65) Prior Publication Data
US 2018/0071218 A1    Mar. 15, 2018

(30) Foreign Application Priority Data
Apr. 1, 2015 (IN) .............................. 380/KOL/2015

(51) Int. Cl.
| | |
|---|---|
| *A61K 9/14* | (2006.01) |
| *A61K 9/00* | (2006.01) |
| *A61K 31/137* | (2006.01) |
| *A61K 31/56* | (2006.01) |
| *A61K 31/58* | (2006.01) |
| *A61K 9/16* | (2006.01) |
| *A61K 47/24* | (2006.01) |
| *A61K 47/26* | (2006.01) |

(52) U.S. Cl.
CPC ............ *A61K 9/145* (2013.01); *A61K 9/0075* (2013.01); *A61K 9/1623* (2013.01); *A61K 31/137* (2013.01); *A61K 31/56* (2013.01); *A61K 31/58* (2013.01); *A61K 47/24* (2013.01); *A61K 47/26* (2013.01); *A61K 2300/00* (2013.01)

(58) Field of Classification Search
CPC .... A61K 9/145; A61K 9/0075; A61K 9/1623; A61K 31/137; A61K 31/56; A61K 31/58; A61K 47/24; A61K 47/26
See application file for complete search history.

(56) References Cited

FOREIGN PATENT DOCUMENTS

| | | |
|---|---|---|
| WO | 2005/041922 A1 | 5/2005 |
| WO | 2013/091006 A1 | 6/2013 |
| WO | 2013/144655 A1 | 10/2013 |
| WO | 2015/035114 A1 | 3/2015 |

OTHER PUBLICATIONS

Portillo et al. (Effects of Rotation Rate, Mixing Angle, and Cohesion in Two Continuous Powder Mixers: a Statistical Approach, 2008 ).*
International Search Report and Written Opinion for International Patent Application No. PCT/IB2016/000418, dated Jul. 1, 2016, 10 pages.

* cited by examiner

*Primary Examiner* — Johann R Richter
*Assistant Examiner* — Genevieve S Alley
(74) *Attorney, Agent, or Firm* — Merchant & Gould P.C.

(57) ABSTRACT

The invention relates to processes for dry powder blending. Specifically the invention relates to dry powder blending of pharmaceutical and non-pharmaceutical solid particulate matter and powders. More specifically the invention relates to dry powder blending of microparticles, and to dry powder blends for use as pharmaceuticals. In particular, the present invention relates to a process of preparing a dry microparticulate powder blend comprising one or more micronized active pharmaceutical ingredient(s) (API) and optionally, one or more micronized or non-micronized pharmaceutically acceptable carrier(s) and/or excipient(s), wherein the process comprises the steps of 'pulsating blending' of the micronized active pharmaceutical ingredient(s) and the pharmaceutically acceptable carrier(s) and/or excipient(s).

31 Claims, 5 Drawing Sheets

PROCESS FOR MANUFACTURING DRY POWDER BLENDS

This is a National Stage Application of International Patent Application No. PCT/IB2016/000418, filed 1 Apr. 2016, which claims benefit of Serial No. 380/KOL/2015, filed 1 Apr. 2015 in India and which applications are incorporated herein by reference. To the extent appropriate, a claim of priority is made to each of the above disclosed applications.

FIELD

The present disclosure relates to processes for dry powder blending. More particularly, the present invention relates to processes for dry powder blending of microparticles and to dry powder blends for use as pharmaceuticals, including a single step production of uniform powder blends. The invention is particularly suited for producing dry powder blends for pulmonary administration.

BACKGROUND

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavor to which this specification relates.

Blending is the process of bringing distinct bulk material particles into close contact to produce a mixture of consistent quality as established by a pre-determined set of criteria. Blending of bulk solids is an important unit operation in many industries e.g., pharmaceuticals, cosmetics, food processing, metallurgy, mining, textiles, dyes, etc. The primary objective of the blending process is to manufacture a homogeneous product. For a homogeneous product it is imperative to inter-disperse particles of similar or diverse properties, uniformly. A mixture can be defined as homogeneous if every sample of the mixture has the same composition and properties as any other. The results can be presented as a standard deviation or relative standard deviation.

In a variety of pharmaceutical and non-pharmaceutical applications considerable effort in terms of resources and time is spent in developing a homogeneous blend. The phenomena of particle segregation and agglomeration present a challenge in developing a reproducible blending process. For dry particle mixing, the cohesive and adhesive forces acting between particles depend on molecular forces. Body forces (or gravitational forces) are proportional to the cube of the particle diameter, while Van der Waals forces are proportional to the particle diameter. Thus, for smaller particles (lesser than 10-20 µm), the inter-particle forces are significantly large compared to the particle weight. However most traditional powder technology applications do not deal with powders smaller than about 20 µm. This challenge is particularly exemplified in applications where the solid particulates to be blended are cohesive or partially cohesive in nature.

Particularly for the pharmaceutical applications and more particularly for pulmonary drug delivery, particles less than 5 µm are desired. This low particle size is required for efficient delivery of the active pharmaceutical ingredient (API) to the deep lungs. These micronized particles are typically manufactured using a dry or wet milling process and the high inter-particle forces due to small particle size make the solid API particulates very cohesive. The cohesive nature of the micronized API poses unique challenges in developing technologies for dry powder delivery of API to the lungs using delivery devices and technologies. At each stage during the dry powder inhaler (DPI) product life e.g., manufacture of the formulation, dose metering in primary package, storage, shipping and delivery to the patient, special methodologies have to be developed to minimize the impact of the cohesive nature of the API. In addition, dosage considerations require a diluent for potent molecules and/or additional excipients for formulation stabilization. As a result, several formulation approaches are utilized and a majority of these aim at improving the powder handling properties by creating blends with larger size particles.

The most common approach is to use particles that are larger or coarser (typically 40-100 µm) than that of the micronized API to act as carriers (e.g., lactose) of the micronized API when brought in contact with each other. The objective of the carrier particles is to improve micronized API flowability, thus improving dosing accuracy and minimizing the dose variability observed with cohesive micronized API alone. The success of this approach is limited by the cohesive and adhesive forces experienced by the particulates. The cohesive forces experienced by the micronized API and the carrier particles have to be overcome to adhere micronized API to the larger carrier particles. Moreover, the adherence of the micronized API has to be uniform throughout the distribution of the carrier particles to minimize blend variability and dose variability. For subsequent delivery of the API to the patient, the adhesive forces between micronized API and carrier particles have to be overcome. This phenomenon is typically facilitated by addition of a fraction of fine carrier particles (typically 1 to 20 µm) in the formulation to release the micronized API from the surface of the large carrier particles.

However, to practically manufacture blends of micronized and/or nano-sized API with micro and/or nano-particulate excipients is technically very challenging. This is due to the inherent cohesive nature of these components in their nascent state. In order to achieve a homogeneous blend the cohesive structures or agglomerates have to be destroyed. This challenge becomes particularly steep when more than one micronized API species has to be uniformly distributed in a blend. Moreover, the diverse and competing physical properties of multiple components make it a statistically improbable to achieve a multi-species homogeneous blend.

The prior art has described mechanical blenders that are available in a variety of operating principles, applications and scale. These include tumbling mixers, convective mixers, fluidized bed mixers, high-shear mixers, including media mills and hammer mills. Despite the plethora of blending hardware options available, manufacture of a homogeneous powder blend remains elusive because of the challenges described earlier.

The current best practice to commercially manufacture a dry powder blend of micronized API, microparticulate excipients and carriers for pulmonary drug delivery involves incorporation of these components in a staggered manner into a high shear blender. The high shear is applied in a continuous manner for prolonged period of time to de-agglomerate the micronized API until an acceptable content uniformity of micronized API in the blend is achieved. Blends of multiple APIs require several blending and processing steps making it technically complex and resource prohibitive.

Longer blending durations (typically ≥30 minutes for one API) are required to adequately de-agglomerate the micronized API and distribute uniformly in the powder bed with the various formulation components. Longer blending times are typically required to incorporate more than one API in the blend. Further, dispersion of particulates in the sub 1 μm range into particulates of 100-200 μm range can take well over 4 hours using conventional methods such as ball mills. However the higher energy input for a prolonged time period may also result in strong adherence of micronized API particles to the larger carrier particles surface. As mentioned earlier, this issue becomes particularly complex when more than one micronized API is present in the blend because of the differential cohesive and adhesive forces of the APIs with respect to the excipient components resulting in varying rates of mixing and transfer to the surface of the carrier particles.

The prolonged input of high shear energy may result in particle damage and mechanical and thermal induced physical and chemical degradation of the micronized API and excipients. Another common manifestation of physicochemical changes due to prolonged high shear is exhibited by deposits of crystallized API(s) and/or excipients on the impeller blades, shaft or walls of the vessel. These deposits, which are primarily agglomerates of the API(s) do not get dislodged from the surfaces through the course of blending. This phenomenon result is significantly altered API content and degradation profile within the formulation. This in exhibited by batch to batch inconsistency and/or batch failure.

Another critical manifestation of altered physico-chemical properties due to prolonged input of high shear is tribo-electric charging. The tribo-electric charging of the dry powder blend is problematic for further handling of the powder during filling operation into the primary containers, emptying properties from the primary container and delivery performance because of the deposition on surfaces of the delivery devices. To dissipate the electrostatic charge built up as a result of the high shear forces applied, the high-shear blended powders are commonly stored at specifically controlled temperature and humidity conditions by controlled exposure to moisture. This process known as "conditioning" or "resting period" or "charge-dissipation" results in an additional cost burden due to time, storage and logistics required.

It is therefore desirable to develop improved processes for blending of micronized and/or nano-sized API, micro or nano-particulate excipients and carrier components, which may address one or more of the disadvantages discussed above. It is further advantageous to produce a uniform powder blend, particularly for particles sized for pulmonary administration, which can be produced in a single step. What is required is a process that overcomes one or more of the problems of the prior art. Such a simplified process reduces the risk of batch to batch inconsistency, batch failure and product loss, minimizes the handling and conditioning stages, thereby reducing the time and cost of the current multi-step blending processes.

SUMMARY OF THE INVENTION

The present invention provides for processes of producing a dry microparticulate powder blend comprising micronized API(s), pharmaceutically acceptable carrier(s) and pharmaceutically acceptable micronized excipient(s), wherein the process comprises of pulsating blending of the micronized API, pharmaceutically acceptable carrier(s) and pharmaceutically acceptable excipient(s), in a single step.

In some embodiments, the present invention provides a process of producing a dry microparticulate powder blend comprising one micronized API and one pharmaceutically acceptable carrier, wherein the process advantageously comprises short pulsating blending of the micronized API and the pharmaceutically acceptable carrier, in a single step.

In some embodiments, the present invention provides a process of producing a dry microparticulate powder blend comprising two or more micronized APIs and one pharmaceutically acceptable carrier, wherein the process advantageously comprises short pulsating blending of the micronized APIs and the pharmaceutically acceptable carrier, in a single step.

In some embodiments, the present invention provides a process of producing a dry microparticulate powder blend comprising one micronized API, one pharmaceutically acceptable carrier and one pharmaceutically acceptable micronized excipient, wherein the process advantageously comprises short pulsating blending of the micronized API, one pharmaceutically acceptable micronized excipient and one pharmaceutically acceptable carrier, in a single step.

In further embodiments, the present invention provides a process of producing a dry microparticulate powder blend comprising two or more micronized APIs, one pharmaceutically acceptable carrier and one pharmaceutically acceptable micronized excipient, wherein the process advantageously comprises short pulsating blending of the micronized APIs, one pharmaceutically acceptable micronized excipient and one pharmaceutically acceptable carrier, in a single step.

In several embodiments, the present invention provides dry microparticulate powder blends comprising of the micronized API and pharmaceutically acceptable carrier and pharmaceutically acceptable micronized excipient, which are suitable for oral pulmonary drug delivery using dry powder inhalers.

In several embodiments, the present invention provides dry microparticulate powder blends comprising the micronized API and pharmaceutically acceptable carrier and pharmaceutically acceptable micronized excipient, which are suitable for direct filling, granulation, coating, compression for oral and topical drug delivery using capsules, tablets, creams, lotions, slurries, suspensions, thin films, microneedles etc.

In several embodiments, the present invention provides a dry microparticulate powder blend for a combination asthma and COPD therapy including a corticosteroid and a beta agonist wherein the dry powder blend is produced in a single step.

In several embodiments, the present invention provides a dry microparticulate powder blend for a combination asthma and COPD therapy including a corticosteroid and a muscarinic antagonist (formerly known as anticholinergic) wherein the dry powder blend is produced in a single step.

In several embodiments, the present invention provides a dry microparticulate powder blend for a combination asthma and COPD therapy including a beta agonist and a muscarinic antagonist (formerly known as anticholinergic) wherein the dry powder blend is produced in a single step.

In several embodiments, the present invention provides a dry microparticulate powder blend for a combination asthma and COPD therapy including a corticosteroid, a beta agonist and a muscarinic antagonist (formerly known as anticholinergic) wherein the dry powder blend is produced in a single step.

In several embodiments, the pharmaceutically acceptable micronized excipient is micronized or fine lactose.

In several embodiments, the pharmaceutically acceptable carrier is microparticulate lactose.

In some embodiments, pharmaceutically acceptable carrier is a dry powder blend of microparticulate lactose.

DETAILED DESCRIPTION OF THE INVENTION

Figure 1:
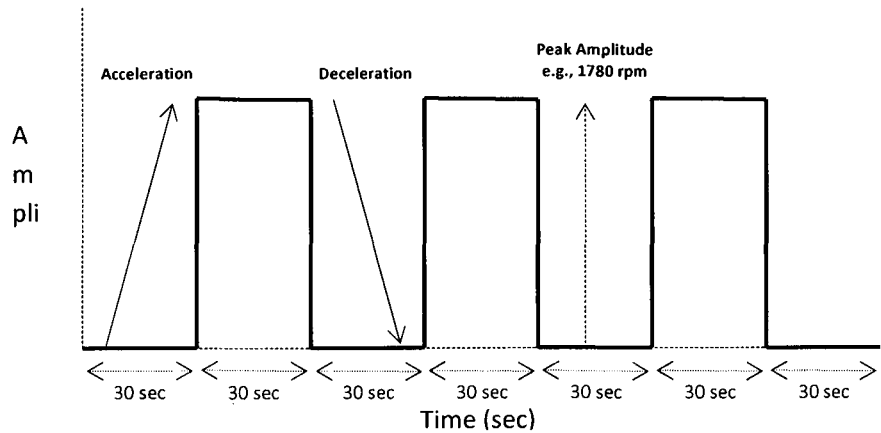
FIGS. 1 to 15 show various acceleration and deceleration phases at different amplitudes and time.

It is intended that the scope of the present invention herein disclosed should not be limited by any particular embodiment described herein. While various embodiments of the present invention have been described above, it should be noted that they have been presented by way of example only, and not limitation. Numerous changes to the disclosed embodiments can be made in accordance with the disclosure herein without departing from the spirit or scope of the invention.

In the present invention significantly improved processes for manufacturing dry microparticulate powder blends comprising micronized API, pharmaceutically acceptable micronized excipient and pharmaceutically acceptable carrier, that have enhanced blend and content uniformity, have been developed. Various embodiments of the present invention advantageously utilize a pulsating blending process to effectively and efficiently de-agglomerate micronized API particles and disperse them in pharmaceutically acceptable carrier and pharmaceutically acceptable micronized excipient. Advantageously, the homogeneous dry microparticulate powder blends are achieved in a single step. Further advantageously, the pulsating blending process prevents prolonged and excessive energy input to the dry microparticulate powder blends.

Effective and efficient de-agglomeration of one or more APIs in the pharmaceutically acceptable carrier and pharmaceutically acceptable micronized excipient, offers enhanced blend and content uniformity, thereby, preventing batch to batch variability and/or batch failure. A single step process to achieve a homogeneous dry microparticulate powder blend offers enhanced control of the manufacturing process while offering cost savings. A homogeneous distribution of one or more APIs in a pharmaceutically acceptable carrier offers enhanced ability to reduce multiple complex blend handling steps and co-formulate multiple APIs in a single dosage form. Reduced cumulative and sustained energy input to achieve a homogeneous dry microparticulate powder blend offers enhanced physical and chemical stability of the dry powder blend by reducing selective and differential losses of API(s) in the blending vessel surfaces e.g., vessel walls, shaft of the impeller, impeller blades etc. thereby, achieving an on-target API content and on the other hand reducing the potential for chemical degradation. Reduced energy input and process handling of the dry microparticulate powder blend offers advantages in dissipating tribo-electric charge thereby obviating the need for "conditioning", enabling easier powder processing and improving delivery performance through delivery devices. The effective de-agglomeration of micronized API particles improves aerodynamic properties for orally inhaled dosage forms, suspendability for injectable or oral dosage forms and improved dispersability for oral dosage forms.

Non-limiting examples of categories of active pharmaceutical ingredients (APIs) include non-steroidal anti-inflammatory agents, corticosteroids, anti-neoplasties, anti-microbial agents, anti-virals, anti-bacterial agents, anti-fungals, anti-asthmatics, bronchodilators, antihistamines, immunosuppressive agents, anti-anxiety agents, sedatives/hypnotics, anti-psychotic agents, anticonvulsants and calcium channel blockers.

Non-limiting examples of the active pharmaceutical ingredients include albuterol, beclomethasone dipropionate, budesonide, calcitonin, formoterol, flunisolide, fluticasone propionate, fluticasone furoate, ipratropium bromide, indacaterol maleate, mometasone, salmeterol xinafoate, tobramycin sulfate, tiotropium bromide, umeclidinium bromide, vilanterol, celecoxib, rofecoxib, docetaxel, paclitaxel, acyclovir, alprazolam, amiodaron, amoxicillin, anagrelide, busulfan, carbamazepine, ceftazidime, cefprozil, ciprofloxacin, clarithromycin, clozapine, cyclosporine, diazepam, estradiol, etodolac, famciclovir, fenofibrate, fexofenadine, gemcitabine, ganciclovir, granulocyte colony-stimulating factor, insulin, itraconazole, lamotrigine, leuprolide, loratidine, lorazepam, meloxicam, mesalamine, minocycline, modafinil, nabumetone, nelfinavir mesylate, olanzapine, oxcarbazepine, parathyroid hormone-related peptides, phenytoin, progesterone, propofol, ritonavir, sirolimus, somatostatin, sulfamethoxazole, sulfasalazine, testosterone, tacrolimus, tiagabine, tizanidine, triamcinolone acetonide, trimethoprim, valsartan, voriconazole, zafirlukast, zileuton and ziprasidone.

The active pharmaceutical ingredient can have a mass median particle size in the range of about 0.1 to about 20 μm, preferably in the range of about 1 μm to about 15 μm, preferably about 1 μm to about 10 μm, preferably about 1 μm to about 5 μm and more preferably about 1 μm to about 4.5 μm. In some embodiments, the mass median particle size of active pharmaceutical ingredient is between about 1.6 μm and about 2.3 μm.

Mass median Particle size is defined as the diameter at which 50% of the particles by mass are larger and 50% are smaller. It can be measured by sieve analysis, laser diffraction, optical counting, sedimentation etc.

Non-limiting examples of the pharmaceutically acceptable carrier include lipids, sugars, amino acids, lactose, glucose, fructose, sucrose, raffinose, mannose, dextrose, trehalose, trileucine, leucine, mannitol, maltitol, xylitol, glycine, sorbitol, erythritol, phosphatidylcholines (e.g., DSPC, DSPE etc.), calcium salts (e.g., calcium chloride, calcium sulfate), iron salts, starches, carbohydrates, cyclodextrins, cellulose, polyoxyethylene sorbitan fatty acid esters and derivatives, thereof.

The pharmaceutically acceptable carrier can have a mass median particle size in the range of about 1 to about 1000 μm, preferably in the range of about 1 μm to about 750 μm, preferably about 1 μm to about 400 μm, preferably about 5 μm to about 200 μm and more preferably about 1 μm to about 5 μm. In some embodiments, the mass median particle size is between about 74-76 μm and about 50-100 μm.

For the purpose of this application coarse lactose and lactose can have the same meaning.

Non-limiting examples of the micronized excipients include lipids, sugars, amino acids, lactose, glucose, fructose, sucrose, raffinose, mannose, dextrose, trehalose, trileucine, leucine, methionine, mannitol, maltitol, xylitol, glycine, sorbitol, erythritol, phosphatidylcholines (e.g., DSPC, DSPE etc.), starches, carbohydrates, cyclodextrins, calcium salts (e.g., calcium chloride, calcium sulfate), iron salts, cellulose, polyoxyethylene sorbitan fatty acid esters and derivatives, thereof.

The micronized excipient can have a mass median particle size in the range of about 0.1 µm to about 100 µm, preferably 1 to 20 µm. In some embodiments, the mass median particle size is between about 20-25 µm and 50-55 µm.

The present invention provides for processes of producing a dry microparticulate powder blend comprising micronized API(s), pharmaceutically acceptable carrier(s) and/or pharmaceutically acceptable micronized excipient(s).

The present invention provides for processes of producing a dry microparticulate powder blend comprising micronized API(s), pharmaceutically acceptable carrier(s) and/or pharmaceutically acceptable micronized excipient(s), wherein the process comprises pulsating blending of the micronized API(s), pharmaceutically acceptable carrier(s) and pharmaceutically acceptable micronized excipient(s), in a single step.

In some embodiments, the present invention provides a process of producing a dry microparticulate powder blend comprising one micronized API, one pharmaceutically acceptable carrier and one pharmaceutically acceptable micronized excipient, wherein the process advantageously comprises short pulsating blending of the micronized API, one pharmaceutically acceptable carrier and one pharmaceutically acceptable micronized excipient, in a single step.

In some embodiments, the present invention provides a process of producing a dry microparticulate powder blend comprising one micronized API and one pharmaceutically acceptable carrier, wherein the process advantageously comprises short pulsating blending of the micronized API and the pharmaceutically acceptable carrier, in a single step.

In some embodiments, the present invention provides a process of producing a dry microparticulate powder blend comprising one micronized API and one pharmaceutically acceptable micronized excipient, wherein the process advantageously comprises short pulsating blending of the micronized API and the pharmaceutically acceptable micronized excipient, in a single step.

In further embodiments, the present invention provides a process of producing a dry microparticulate powder blend comprising two or more micronized APIs, one pharmaceutically acceptable carrier and one pharmaceutically acceptable micronized excipient, wherein the process advantageously comprises short pulsating blending of the micronized APIs, one pharmaceutically acceptable carrier and one pharmaceutically acceptable micronized excipient, in a single step.

In some embodiments, the present invention provides a process of producing a dry microparticulate powder blend comprising two or more micronized APIs and one pharmaceutically acceptable carrier, wherein the process advantageously comprises short pulsating blending of the micronized APIs and the pharmaceutically acceptable carrier, in a single step.

In some embodiments, the present invention provides a process of producing a dry microparticulate powder blend comprising two or more micronized APIs and one pharmaceutically acceptable micronized excipient, wherein the process advantageously comprises short pulsating blending of the micronized APIs and the pharmaceutically acceptable micronized excipient, in a single step.

In some embodiments, the present invention provides a process of producing a dry microparticulate powder blend comprising micronized API(s) and two pharmaceutically acceptable carriers, wherein the process advantageously comprises short pulsating blending of the micronized APIs and the pharmaceutically acceptable carriers, in a single step.

In some embodiments, the present invention provides a process of producing a dry microparticulate powder blend comprising micronized API(s) and two pharmaceutically acceptable micronized excipients, wherein the process advantageously comprises short pulsating blending of the micronized APIs and the pharmaceutically acceptable micronized excipients, in a single step.

The dry powder blends of the present invention are suitable for, without limitation, direct filling, granulation, coating, compression for oral and topical drug delivery using capsules, tablets, creams, lotions, slurries, suspensions, thin films or micro-needles.

Pulsating Blending Process:

'Pulsating blends' are defined as blends that are manufactured by alternating and continuous acceleration and deceleration steps of a dry microparticulate powder bed for a predetermined number of cycles. The acceleration step involves an abrupt movement of the microparticulate dry powder bed from the position of rest to a higher velocity of the microparticulate components of the powder bed. The acceleration step is achieved by a high shear blender with a shaft and a blade, the rotational speed of which is increased from a resting position (Blade speed=0 rpm; Blade tip speed=0 meters/second) to an accelerated position (Blade rotational speed=>0 rpm; Blade tip speed=>0 meters/second). In several embodiments, the blade rotational speed ranges from about 1 rpm to about 2000 rpm preferably from about 100 rpm to about 1700 rpm, 400 rpm to about 1400 rpm, and about 700 rpm to about 1100 rpm. In some embodiments the blade rotational speed ranges from about 500 to about 2000 rpm and the blade tip speed ranges from about 0.5 meter/second to about 15 meters/second and preferably about 4.5 meters/second to about 20.0 meters/second.

The deceleration step involves an abrupt decrease in the velocity of the microparticulate dry powder bed resulting in a decrease in the velocity of the microparticulate components of the powder bed. The deceleration step is achieved by decreasing the rotational speed of a blade from an accelerated position to a substantially lower rate. Through the course of the deceleration, rotational speed of the blade can achieve a complete stop (i.e., 0 rpm) or a substantially lower rotational speed defined as less than about 20%, 15%, 10% or 5% (e.g., 0, 10 and 50 rpm) of the peak amplitude speed in rpm. The deceleration step can also be viewed as a 'resting period' for the microparticulate dry powder blend. In several embodiments, the blade is decelerated from about 2000, 1900 1800, 1700, 1600, 1500, 1400, 1300, 1200, 1100, 1000, 900, 800, 700, 600 500, 400, 300, 200 and 100 rpm to 0 rpm. In other embodiment, the blade is decelerated from about 2000, 1900, 1980, 1780, 1500, 1000 and 500 rpm to 0 rpm In other embodiment, the blade is decelerated from about 1780, 1500, 1000 and 500 rpm to 10 rpm.

The absolute peak amplitude of the acceleration process can be tailored to the physico-chemical properties of the microparticulate dry powder blend and the properties of the individual components of the microparticulate dry powder blend. The peak amplitude can range from 500 to 2000 rpm (e.g., 500, 1000, 1500, 1780, 1900, 2000 rpm). However, the trough amplitude is maintained at least less than about 20%, 15%, 10%, or 5% of the peak amplitude speed in rpm or more typically the trough amplitude is maintained at least less than about 100 rpm, 50 rpm, 30 rpm or 10 rpm of the peak amplitude speed.

The peak amplitude of the acceleration process can be tailored to the physico-chemical properties of the microparticulate dry powder blend and the properties of the individual components of the microparticulate dry powder blend and is maintained ranging from 10 seconds to 60 seconds (e.g., 10, 20, 30, 40, 50 and 60 seconds). The trough amplitude (0 or non-zero rpm) is maintained from 10-180 seconds (e.g., 10, 20, 30, 40, 50 and 60, 90, 150, 180, 210 and 240 seconds). In one embodiment, a peak amplitude of 1500 rpm is maintained for 10 seconds followed by trough amplitude (0 rpm) for 10 seconds. In another embodiment, a peak amplitude of 1500 rpm is maintained for 10 seconds followed by trough amplitude (0 rpm) for 60 seconds. In yet another embodiment, a peak amplitude of 1500 rpm is maintained for 30 seconds followed by trough amplitude (0 rpm) for 10 seconds. Accordingly, symmetrical or asymmetrical pulsating blends can be manufactured.

The peak amplitude of the acceleration process can be modulated through the course of the blending process, wherein, a peak amplitude (P) of the acceleration process for time 'T' is followed by a deceleration step with a trough amplitude (D) for time 'T'; followed by an acceleration process at a peak amplitude lower than P (i.e. P−x) for time 'T'; followed by a deceleration step with a trough amplitude (D) for time 'T'. The peak amplitude of the acceleration process can also be modulated through the course of the blending process, wherein, a peak amplitude (P) of the acceleration process for time 'T' is followed by a deceleration step with a trough amplitude (D) for time 'T'; followed by an acceleration process at a peak amplitude lower than P (i.e. P−x) for a shorter time (i.e. T−y); followed by a deceleration step with a trough amplitude (D) for time 'T'. Several embodiments with different amplitudes, pulse width modulation with pulse time 'T', pulse frequency 'F' and combinations thereof are presented herein.

Components of the microparticulate powder bed experience a differential increase in velocity as a result of the acceleration step. Similarly, the components experience a differential decrease in velocity as a result of the deceleration step. Advantageously, the pulsating blends achieve a high cumulative number of velocity gradients through the pulsating process. Advantageously, the pulsating blends impart lower cumulative energy to the microparticulate dry powder blends leading to the advantages highlighted earlier. Advantageously, the short pulsing waves minimize segregation mechanisms as exhibited by enhanced blend and content uniformity (Table 1 through 7).

Advantageously, the Pulsating blends can be utilized for blending compressible and non-free flowing powders (i.e. powders with a Hausner Ratio ≥1.6; wherein Hausner Ratio is the ratio of compacted density/bulk density), combination of non-compressible and free flowing powders (i.e. powders with a Hausner Ratio <1.6) and combinations of compressible and non-compressible powders (i.e. blends with individual components with Hausner Ratios between 0.1-5.0) in different ratios.

Flash Blends:

Flash Blend is a type of Pulsating Blend with a very short span of time. 'Flash blends' are defined as blends in which pre-determined acceptable blend uniformity (BU) is advantageously achieved in a 'short span of time'. The BU requirement is typically characterized by a percentage relative standard deviation (% RSD) which is less than or equal to 3% (≤3%). The 'short span of time' is, advantageously, assigned at less than or equal to 4 minutes (≤4 minutes).

To manufacture the blend, half the quantity of pharmaceutically acceptable carrier was added to blending vessel followed by sieved/unsieved microparticulate API(s) & finally the remaining quantity of carrier. The vessel was closed. The amplitude of blades was increased & then decreased for specific time period & the process was repeated for specific number of pulses before opening the vessel. The blending vessel is usually charged or loaded, from about 10% to about 80% of its volume, preferably about 20% to about 70% of its volume more preferably 50% of its volume.

A high-shear mixer mixes, one or more ingredients with another ingredients homogenously with which it would normally be immiscible.

Non-Limiting Examples of Blending Equipment:

Different types of blending equipment were utilized moreover these are not limiting examples of blenders or mixers which can be used for the invention:

1. Blender 1: In some embodiments a ProPrep® Chopper Grinder Model WCG75 (Waring Commercial, Torrington, Conn. 06790) was used with a 0.7 L vessel volume.
2. Blender 2: In another set of embodiments a Diosna High Shear Mixer (Diosna, Osnabruck, Germany) was used with a 1 L and 2 L vessel volume.

Additionally one can use GEA PharmaConnect® High Shear Mixer with TRV modules (GEA Process Engineering, Columbia, Md., USA) with varying volume of a 5 L and 30 L vessel.

API:

Two different types of micorparticulate API were utilized.

1. API 1 [Fluticasone Propionate (FP)]. Two different particle size distributions (PSD) were investigated. In some embodiments API 1 with ×10: 0.7 µm, ×50: 1.6 µm and ×90: 3.4 µm was utilized to prepare microparticulate blends. In other embodiments API 1 with ×10: 1.1 µm, ×50: 2.3 µm and ×90: 4.2 µm was utilized to prepare microparticulate blends. For API 1 the ×10 can range from 0.5-1.5 µm, ×50 from 1.0-4.5 µm, and ×90 from 3.5-8.5 µm.
2. API 2 [Salmeterol Xinafoate (SX)]. Two different particle size distributions (PSD) were investigated. In some embodiments API 2 with ×10: 0.8 µm, ×50: 2.0 µm and ×90: 4.2 µm was utilized to prepare microparticulate blends. In other embodiments API 2 with ×10: 0.9 µm, ×50: 2.3 µm and ×90: 4.7 µm was utilized to prepare microparticulate blends. For API 2 the ×10 can range from 0.5-1.5 µm, ×50 from 1.0-4.5 µm, and ×90 from 3.5-8.5 µm.

Pharmaceutically Acceptable Carrier:

Coarse lactose, Lactohale 200 (LH 200; DFE Pharma, Goch, Germany) with a PSD of ×10: 9 µm, ×50: 74 µm and ×90: 156 µm was utilized to prepare microparticulate blends.

Blend Strengths:

Five different blends strengths were manufactured:

1. API 1 and Carrier: In some embodiments API 1 was blended with carrier, lactose at a concentration of 0.8% w/w of API 1 in the blend.
2. API 2 and Carrier: In some embodiments API 2 was blended with carrier, lactose at a concentration of 0.6% w/w of API 2 in the blend.
3. API 1, API 2 and Carrier: In some embodiments API 1 and API 2 was blended with carrier, lactose at a concentration of 0.8% w/w of API 1 and 0.6% w/w of API 2 in the blend.
4. API 1, API 2 and Carrier: In some embodiments API 1 and API 2 was blended with carrier, lactose at a concentration of 2.0% w/w of API 1 and 0.6% w/w of API 2 in the blend.
5. API 1, API 2 and Carrier: In some embodiments API 1 and API 2 was blended with carrier, lactose at a concentration of 4.0% w/w of API 1 and 0.6% w/w of API 2 in the blend.

Blend Manufacturing Process:
1. To manufacture the blend,
    a. In one embodiment, the microparticulate API 1 and API 2 were passed through a coarse sieve. Pharmaceutically acceptable carrier (coarse lactose; 50% of the target amount) was charged to the blending vessel. The sieved API 1 and 2 were charged on top of the coarse lactose bed. The remaining quantity of the coarse lactose was then charged to the vessel. The vessel lid was closed.
    b. In another embodiment, the microparticulate API 1 and API 2 were used, as is, i.e. without sieving. Pharmaceutically acceptable carrier (coarse lactose; 50% of the target amount) was charged to the blending vessel. The API 1 and 2 were charged on top of the coarse lactose bed. The remaining quantity of the coarse lactose was then charged to the vessel. The vessel lid was closed.
    c. In another embodiment, the microparticulate API 1 and API 2 along with coarse lactose were charged to the blending vessel and the lid was closed.
2. In several embodiments the percentage loading of the vessel was varied from nominally 12% to 72% (e.g., 12, 14, 24, 50, 66 and 72%).
3. The blade angle in the vessels ranged from 0° to 41° (e.g., 0°, 36°, and 41°).
4. The amplitude of the blades was increased for a specified time period, decreased for a specified time period and the process was repeated for a pre-determined number of 'pulses' prior to opening the vessel lid for withdrawing the samples.

Blend Sampling Apparatus and Process:

Microparticulate blends were sampled using a MicroThief (Sampling Systems, Sweeny, Tex., USA). For each microparticulate blend, ten samples of nominally 13 mg from different locations of the powder bed were retrieved.

Visual Analysis of Blending Equipment:

Microparticulate blends were visually observed for agglomeration, powder deposition on blender body or blades, and any color change.

Assay and Blend Uniformity (BU) Analysis:

Microparticulate blends were analyzed for assay of API 1, API 2 and blend uniformity analysis using ultra-high performance liquid chromatography (UPLC) with ultraviolet (UV) detection at 228 nm. The method utilized an Acquity UPLC H-Class with UV Detector (Milford, Mass., USA) with a Waters Acquity BEH C8 100×2.1 mm, 1.7 µm (Milford, Mass., USA) column. The method utilized a mobile phase comprising of water:acified methanol (97:3; v/v) and acetonitrile:acified methanol (97:3; v/v), with a flow rate of 0.5 mL/min, column temperature of 50° C., injection volume of 5 µL and run time of 4.6 minutes. API 1 and API 2 were quantitated using a reference standard with the retention time of API 1 and API 2 being 1.1 minutes and 2.3 minutes, respectively. Microparticulate blend samples were prepared for assay and BU analysis by using water:methanol (50:50, v/v) as the dilution media. The assay results for API 1 and API 2 are reported as percentage (%) recovery of the theoretical content of the API(s). The % recovery values for FP and SX ranged from 88 to 110%. The blend uniformity (BU) results are reported as a percentage relative standard deviation (% RSD) calculated from 10 samples retrieved from each microparticulate powder blend condition and time point.

Blends:

In embodiments 1 through 3 (Table 1) binary blends of API 1 and coarse carrier (LH 200) manufactured using Blender 1 at 0.7 L vessel volume with the pulsating blending process are described. These blends represent a constant strength (strength 1) and PSD of one API (API 1) with various pulsating cycles conceptually represented in FIG. 1. Acceptable blend uniformity was achieved in as little as two pulsating cycles. In addition, acceptable BU was achieved with these flash blends (≤3 minutes).

In embodiments 4 through 6 (Table 2) binary blends of API 2 and coarse carrier (LH 200) manufactured using Blender 1 at 0.7 L vessel volume with the pulsating blending process are described. These blends represent a constant strength (strength 2) and PSD of a different API (API 2) with various pulsating cycles conceptually represented in FIG. 1. Acceptable blend uniformity was achieved in as little as two pulsating cycles. In addition, acceptable BU was achieved with these flash blends (≤3 minutes).

In embodiments 7 through 11 (Table 3) ternary blend of API 1, API 2 and coarse carrier (LH 200) manufactured using Blender 1 at 0.7 L vessel volume with the pulsating blending process are described. These blends represent a constant strength (strength 3) of the ternary blend with different API 1 and API 2 combinations and different blend batch sizes (100-300 grams) with various pulsating cycles conceptually represented in FIG. 1. Acceptable blend uniformity was achieved in as little as two pulsating cycles. In addition, acceptable BU was achieved with these flash blends (≤3 minutes).

In embodiments 12 through 14 (Table 4) ternary blend of API 1, API 2 and coarse carrier (LH 200) manufactured using Blender 1 at 0.7 L vessel volume with the pulsating blending process are described. These blends represent a constant blend batch size (100 grams) and constant API 1 and API 2 combinations with different strengths (strength 3, 4 and 5) of the ternary blend with various pulsating cycles conceptually represented in FIG. 1. Acceptable blend uniformity was achieved in as little as two pulsating cycles. In addition, acceptable BU was achieved with these flash blends (≤3 minutes).

Figure 2:
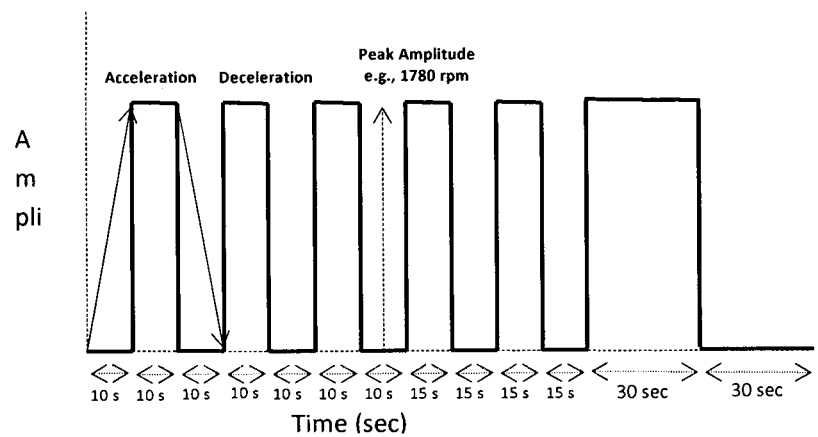
Figure 3:
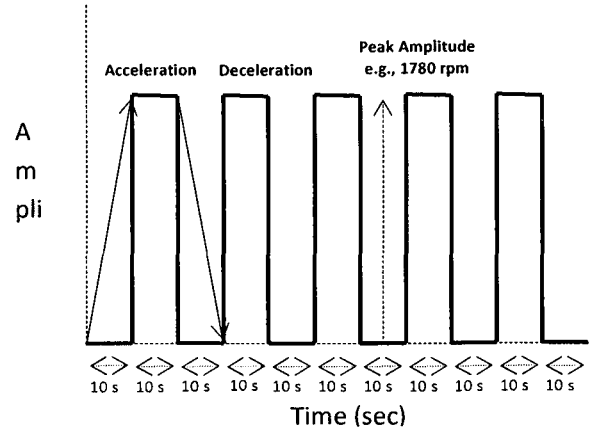
Figure 4:
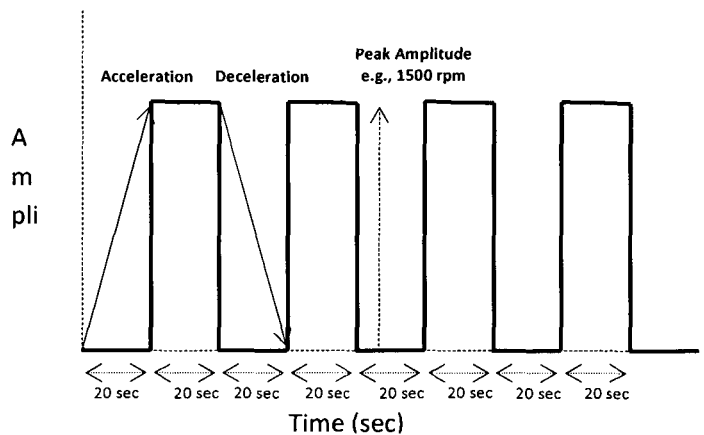
Figure 5:
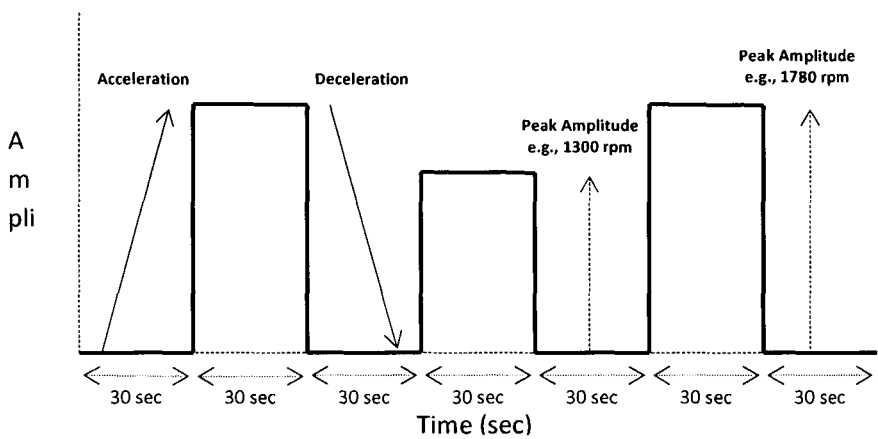
Figure 6:
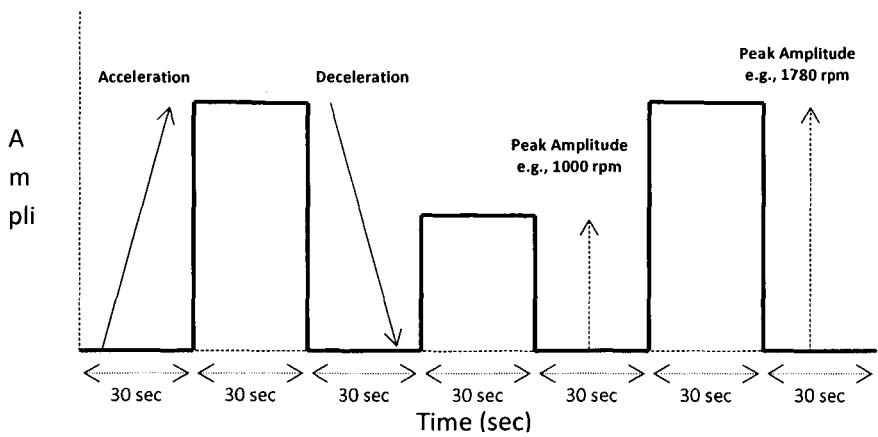
Figure 7:
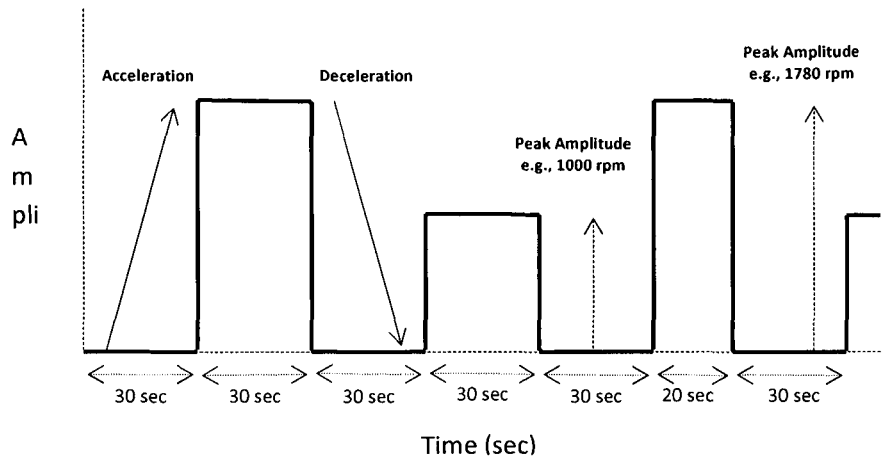
Figure 8:
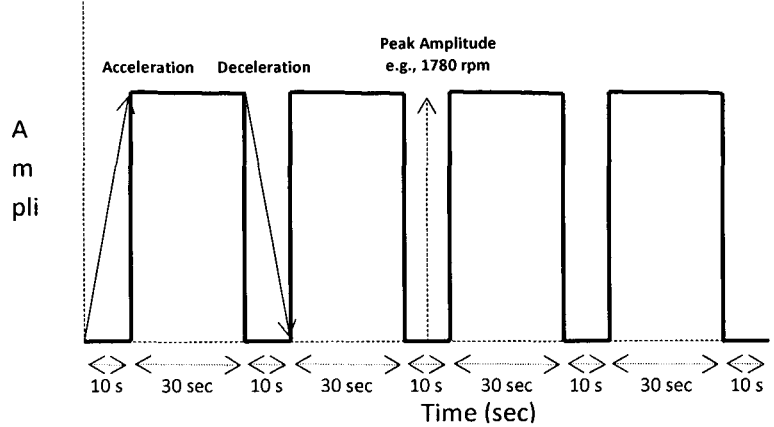
Figure 9:
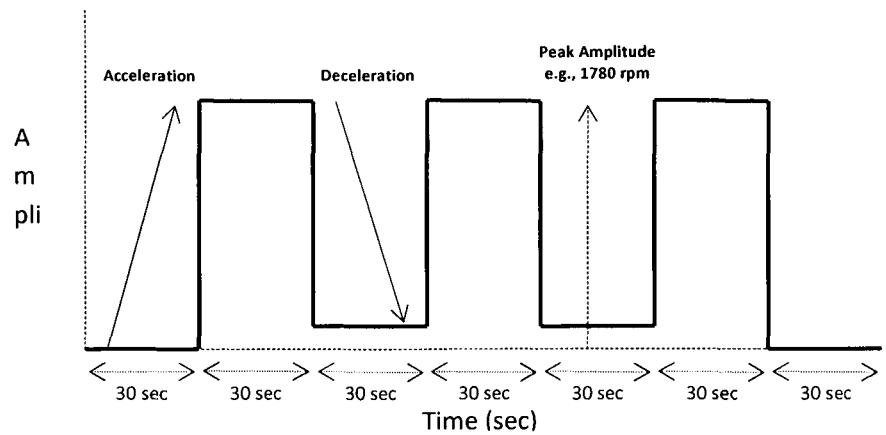
Figure 10:
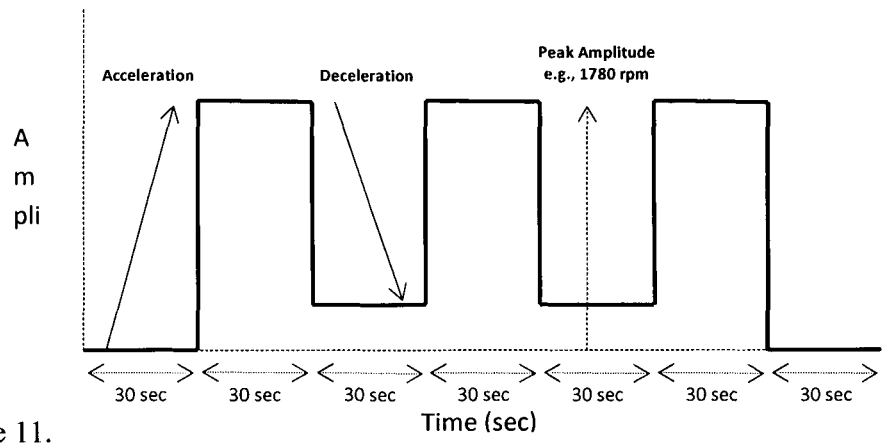
Figure 11:
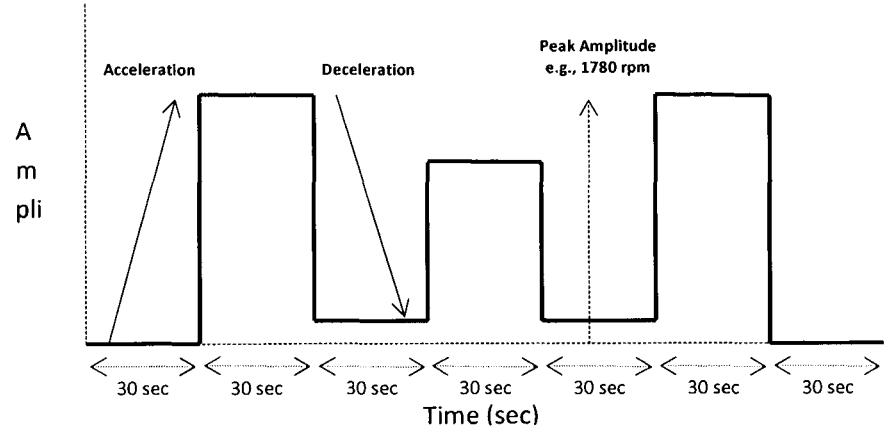
Figure 12:
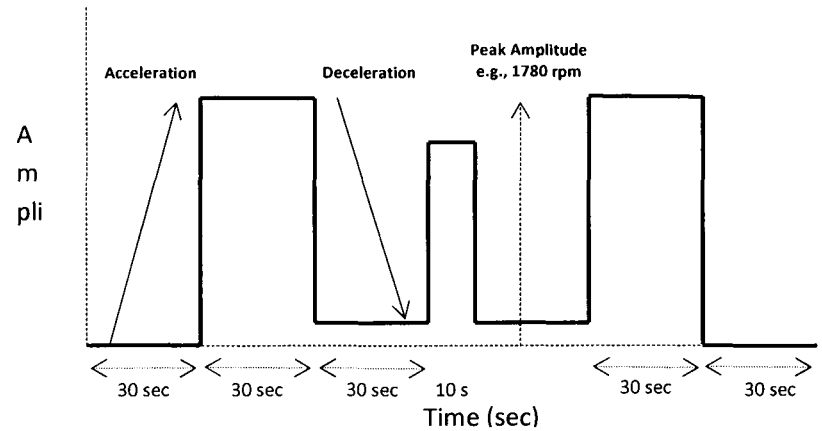
Figure 13:
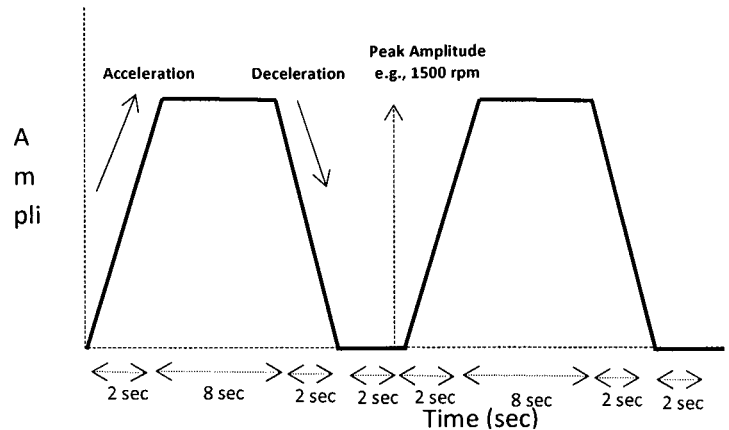
Figure 14:
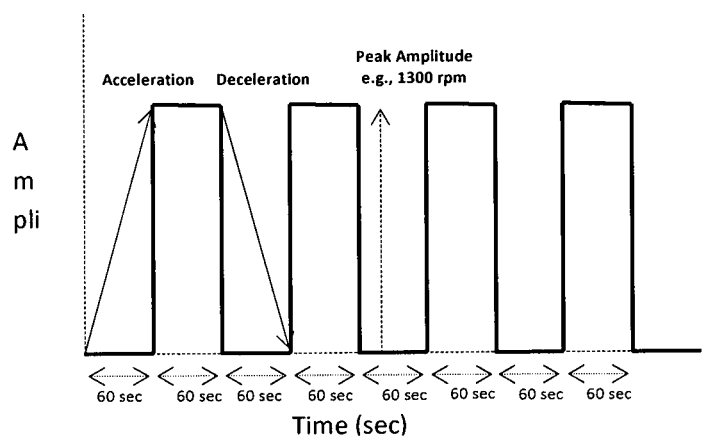
Figure 15:
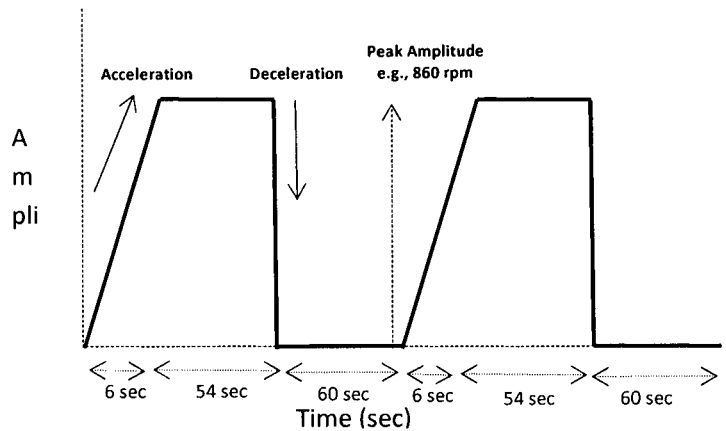

In embodiments 15 through 17 (Table 5) ternary blend of API 1, API 2 and coarse carrier (LH 200) manufactured using Blender 1 at 0.7 L vessel volume with the pulsating blending process are described. These blends represent a constant strength (strength 3) of the ternary blend with constant API 1 and API 2 combinations and different blend batch sizes (100-300 grams) and different pulsating cycles conceptually represented in FIGS. 1 and 2. Acceptable blend uniformity was achieved within few pulsating cycles. In addition, acceptable BU was achieved with these flash blends (≤3 minutes). These blends also demonstrate the phenomenon of de-mixing of the blends beyond the optimum pulsating cycles. The optimum pulsating cycles are determined for the variables comprising of API PSD, blend batch size and blending speed (rpm).

In embodiments 18 through 20 (Table 6) ternary blend of API 1, API 2 and coarse carrier (LH 200) manufactured using Blender 2 at 1.0 L and 2.0 L vessel volume with the pulsating blending process are described. These blends represent a constant strength (strength 3) of the ternary blend with a second blender (Blender 2), different blending speed from Blender 1, different API 1 and API 2 combinations, different blend batch sizes (300-600 grams) and different pulsating cycles conceptually represented in FIGS. 1 and 2. Acceptable blend uniformity was achieved within few pulsating cycles. In addition, acceptable BU was achieved with these flash blends (≤3 minutes).

In embodiments 21 through 23 (Table 7) ternary blend of API 1, API 2 and coarse carrier (LH 200) manufactured using Blender 2 at 2.0 L vessel volume with the pulsating blending process are described. These blends represent a constant strength (strength 3) of the ternary blend, constant API 1 and API 2 combinations and constant blend batch size (600 grams) with a second blender (Blender 2), different blending speed from Blender 1 and within Blender 2 (500-1500 rpm) and different pulsating cycles conceptually represented in FIGS. 1 and 2. Acceptable blend uniformity was achieved within few pulsating cycles. In addition, acceptable BU was achieved with these flash blends (≤3 minutes). These blends also demonstrate the phenomenon of optimizing pulsating cycles with blending speed (rpm), API PSD and blend batch size.

In embodiments 24 through 28 (Table 8) binary and ternary blends of API 1, API 2 and coarse carrier (LH 200) manufactured using a third blender (Blender 3) at 5.0 L vessel volume with the pulsating blending process are described. These blends represent a constant strength: strength 6 for embodiment 24; strength 2 for embodiment 25 and strength 3 for embodiments 26 through 28. These embodiments represent different blend batch sizes (1475 to 1670 grams), different blending speeds from Blenders 1 and 2 and within Blender 3 (800-1979 rpm) and different pulsating cycles conceptually represented in FIGS. 1, 3, 4, 14 and 15. Acceptable blend uniformity was achieved within few pulsating cycles. In addition, acceptable BU was achieved with these flash blends (≤4 minutes). These blends also demonstrate the phenomenon of optimizing pulsating cycles with blending speed (rpm), API PSD and blend batch size.

In embodiments 29 through 32 (Table 9) ternary blends of API 1, API 2 and coarse carrier (LH 200) manufactured using a third blender (Blender 3) at 30.0 L vessel volume with the pulsating blending process are described. These blends represent a constant strength (strength 3) of the ternary blend, constant API 1 and API 2 combinations with different and large blend batch sizes (7250-10000 grams), different blending speed from Blender 1 and 2 and within Blender 3 (700-860 rpm) and different pulsating cycles conceptually represented in FIGS. 1, 3, 4, 14 and 15. Acceptable blend uniformity was achieved within few pulsating cycles. In addition, acceptable BU was achieved with these flash blends (≤4 minutes). These blends also demonstrate the phenomenon of optimizing pulsating cycles with blending speed (rpm), API PSD and large blend batch sizes.

FIGS. 1 through 13, represent conceptual embodiments of the process for manufacturing microparticulate powder blends using the 'Pulsating' and 'Flash' process. Each embodiment is characterized by an acceleration phase followed by a deceleration phase. Several embodiments with conceptually different amplitudes, pulse width modulation with pulse time, pulse frequency and combinations thereof are presented.

Tables:

TABLE 1

Binary blends of API 1 (Fluticasone Propionate) and coarse carrier (Lactose LH 200) using Blender 1 at 0.7 L vessel volume with the 'Pulsating' blending process.

| | | | | | | Blending | | Blend Parameters | | | |
|---|---|---|---|---|---|---|---|---|---|---|---|
| Blend Embodiment | Blend Strength | API PPS (µm) X10 | API PPS (µm) X50 | API PPS (µm) X90 | Vessel Loading (%) | Batch Size (grams) | Speed Peak Amplitude (RPM) | Sampling Time Point (sec) | BU % RSD | Assay % of Theoretical | Acceleration Pulse (sec) | Deceleration Pulse (sec) | Total no. of Pulse Cycles |
| 1 | 2 | 0.7 | 1.6 | 3.4 | 14 | 60 | 1780 | 60 | 1.5 | 98 | 30 | 30 | 2 |
| | | | | | | | | 120 | 1.4 | 96 | 30 | 30 | 4 |
| | | | | | | | | 180 | 0.7 | 95 | 30 | 30 | 8 |
| 2 | 2 | 0.7 | 1.6 | 3.4 | 14 | 60 | 1780 | 60 | 1.2 | 98 | 30 | 30 | 2 |
| | | | | | | | | 120 | 2.9 | 99 | 30 | 30 | 4 |
| | | | | | | | | 180 | 2.0 | 98 | 30 | 30 | 8 |
| 3 | 2 | 0.7 | 1.6 | 3.4 | 72 | 300 | 1780 | 60 | 1.0 | 102 | 30 | 30 | 2 |
| | | | | | | | | 120 | 0.5 | 101 | 30 | 30 | 4 |
| | | | | | | | | 180 | 1.2 | 97 | 30 | 30 | 8 |

TABLE 2

Binary blends of API 2 (Salmeterol Xinafoate) and coarse carrier (Lactose LH 200) using Blender 1 at 0.7 L vessel volume with the 'Pulsating' blending process.

| | | | | | | Blending | | Blend Parameters | | | |
|---|---|---|---|---|---|---|---|---|---|---|---|
| Blend Embodiment | Blend Strength | API PPS (µm) X10 | API PPS (µm) X50 | API PPS (µm) X90 | Vessel Loading (%) | Batch Size (Grams) | Speed Peak Amplitude (RPM) | Sampling Time Point (sec) | BU % RSD | Assay % of Theoretical | Acceleration Pulse (sec) | Deceleration Pulse (sec) | Total no. of Pulse Cycles |
| 4 | 1 | 0.8 | 2.0 | 4.2 | 12 | 50 | 1780 | 60 | 1.9 | 97 | 30 | 30 | 2 |
| | | | | | | | | 120 | 1.0 | 98 | 30 | 30 | 4 |
| | | | | | | | | 180 | 1.4 | 95 | 30 | 30 | 8 |
| 5 | 1 | 0.8 | 2.0 | 4.2 | 12 | 50 | 1780 | 60 | 5.4 | 100 | 30 | 30 | 2 |
| | | | | | | | | 120 | 6.9 | 99 | 30 | 30 | 4 |
| | | | | | | | | 180 | 3.4 | 95 | 30 | 30 | 8 |

TABLE 2-continued

Binary blends of API 2 (Salmeterol Xinafoate) and coarse carrier (Lactose LH 200) using Blender 1 at 0.7 L vessel volume with the 'Pulsating' blending process.

| | | | | | | Blending | | Blend Parameters | | | | |
|---|---|---|---|---|---|---|---|---|---|---|---|---|
| Embodiment | Blend Strength | API PPS (μm) X10 | X50 | X90 | Vessel Loading (%) | Batch Size (Grams) | Speed Peak Amplitude (RPM) | Sampling Time Point (sec) | BU % RSD | Assay % of Theoretical | Acceleration Pulse (sec) | Deceleration Pulse (sec) | Total no. of Pulse Cycles |
| 6 | 1 | 0.8 | 2.0 | 4.2 | 72 | 300 | 1780 | 60 | 2.3 | 102 | 30 | 30 | 2 |
| | | | | | | | | 120 | 0.8 | 101 | 30 | 30 | 4 |
| | | | | | | | | 180 | 1.3 | 100 | 30 | 30 | 8 |

TABLE 3

Ternary blend of API 1 (Fluticasone Propionate), API 2 (Salmeterol Xinafoate) and coarse carrier (Lactose LH 200) using Blender 1 at 0.7 L vessel volume with the 'Pulsating' blending process.

| Embodiment | Blend Strength | API 1 PPS (μm) X10 | X50 | X90 | API 2 PPS (μm) X10 | X50 | X90 | Vessel Loading (%) | Batch Size (grams) | Blending Speed Peak Amplitude (RPM) | Sampling Time Point (sec) | API 1 BU % RSD |
|---|---|---|---|---|---|---|---|---|---|---|---|---|
| 7 | 3 | 0.7 | 1.6 | 3.4 | 0.8 | 2.0 | 4.2 | 24 | 100 | 1780 | 60 | 1.1 |
| | | | | | | | | | | | 120 | 1.0 |
| | | | | | | | | | | | 180 | 1.2 |
| 8 | 3 | 0.7 | 1.6 | 3.4 | 0.9 | 2.3 | 4.7 | 24 | 100 | 1780 | 60 | 9.0 |
| | | | | | | | | | | | 120 | 2.3 |
| | | | | | | | | | | | 180 | 2.1 |
| 9 | 3 | 1.1 | 2.3 | 4.2 | 0.8 | 2.0 | 4.2 | 24 | 100 | 1780 | 60 | 1.1 |
| | | | | | | | | | | | 120 | 2.6 |
| | | | | | | | | | | | 180 | 4.3 |
| 10 | 3 | 1.1 | 2.3 | 4.2 | 0.9 | 2.3 | 4.7 | 24 | 100 | 1780 | 60 | 2.3 |
| | | | | | | | | | | | 120 | 1.0 |
| | | | | | | | | | | | 180 | 2.2 |
| 11 | 3 | 0.7 | 1.6 | 3.4 | 0.9 | 2.3 | 4.7 | 72 | 300 | 1780 | 60 | 2.1 |
| | | | | | | | | | | | 120 | 1.7 |
| | | | | | | | | | | | 180 | 2.0 |

| Embodiment | API 2 BU % RSD | API 1/API 2 % of Theoretical | API 1 Assay % of Theoretical | API 2 Assay % of Theoretical | Acceleration Pulse (sec) | Deceleration Pulse (sec) | Total # of Pulse Cycles |
|---|---|---|---|---|---|---|---|
| 7 | 1.1 | 99 | 91 | 92 | 30 | 30 | 2 |
| | 1.3 | 98 | 92 | 93 | 30 | 30 | 4 |
| | 0.9 | 99 | 92 | 93 | 30 | 30 | 8 |
| 8 | 1.9 | 103 | 94 | 95 | 30 | 30 | 2 |
| | 2.6 | 100 | 93 | 95 | 30 | 30 | 4 |
| | 2.3 | 100 | 93 | 94 | 30 | 30 | 8 |
| 9 | 2.7 | 99 | 100 | 97 | 30 | 30 | 2 |
| | 2.3 | 100 | 97 | 97 | 30 | 30 | 4 |
| | 4.0 | 100 | 95 | 96 | 30 | 30 | 8 |
| 10 | 1.7 | 100 | 89 | 90 | 30 | 30 | 2 |
| | 0.9 | 99 | 88 | 88 | 30 | 30 | 4 |
| | 2.1 | 100 | 89 | 89 | 30 | 30 | 8 |
| 11 | 1.7 | 101 | 99 | 99 | 30 | 30 | 2 |
| | 1.1 | 101 | 96 | 97 | 30 | 30 | 4 |
| | 1.9 | 101 | 95 | 96 | 30 | 30 | 8 |

TABLE 4

Ternary blends of API 1 (Fluticasone Propionate), API 2(Salmeterol Xinafoate) and coarse carrier (Lactose LH 200) using Blender 1 at 0.7 L vessel volume with the 'Pulsating' blending process.

| Embodiment | Blend Strength | API 1 PPS (μm) | | | API 2 PPS (μm) | | | Vessel Loading (%) | Batch Size (grams) | Blending Speed Peak Amplitude (RPM) | Sampling Time Point (sec) | API 1 BU % RSD |
|---|---|---|---|---|---|---|---|---|---|---|---|---|
|  |  | X10 | X50 | X90 | X10 | X50 | X90 |  |  |  |  |  |
| 12 | 3 | 0.7 | 1.6 | 3.4 | 0.8 | 2.0 | 4.2 | 24 | 100 | 1780 | 60 | 7.1 |
|  |  |  |  |  |  |  |  |  |  |  | 120 | 1.2 |
|  |  |  |  |  |  |  |  |  |  |  | 180 | 1.0 |
| 13 | 4 | 0.7 | 1.6 | 3.4 | 0.8 | 2.0 | 4.2 | 24 | 100 | 1780 | 60 | 1.1 |
|  |  |  |  |  |  |  |  |  |  |  | 120 | 1.0 |
|  |  |  |  |  |  |  |  |  |  |  | 180 | 1.0 |
| 14 | 5 | 0.7 | 1.6 | 3.4 | 0.8 | 2.0 | 4.2 | 24 | 100 | 1780 | 60 | 1.4 |
|  |  |  |  |  |  |  |  |  |  |  | 120 | 0.8 |
|  |  |  |  |  |  |  |  |  |  |  | 180 | 0.9 |

| Embodiment | API 2 BU % RSD | API 1/API 2 % of Theoretical | API 1 Assay % of Theoretical | API 2 Assay % of Theoretical | Acceleration Pulse (sec) | Deceleration Pulse (sec) | Total # of Pulse Cycles |
|---|---|---|---|---|---|---|---|
| 12 | 2.1 | 103 | 100 | 98 | 30 | 30 | 2 |
|  | 1.0 | 100 | 97 | 97 | 30 | 30 | 4 |
|  | 1.2 | 100 | 95 | 95 | 30 | 30 | 8 |
| 13 | 1.0 | 100 | 97 | 97 | 30 | 30 | 2 |
|  | 1.1 | 101 | 96 | 96 | 30 | 30 | 4 |
|  | 1.0 | 100 | 96 | 96 | 30 | 30 | 8 |
| 14 | 1.4 | 100 | 98 | 98 | 30 | 30 | 2 |
|  | 0.7 | 100 | 96 | 96 | 30 | 30 | 4 |
|  | 0.8 | 101 | 97 | 96 | 30 | 30 | 8 |

TABLE 5

Ternary blends of API 1 (Fluticasone Propionate), API 2(Salmeterol Xinafoate) and coarse carrier (Lactose LH 200) using Blender 1 at 0.7 L vessel volume with the 'Pulsating' blending process.

| Embodiment | Blend Strength | API 1 PPS (μm) | | | API 2 PPS (μm) | | | Vessel Loading (%) | Batch Size (grams) | Blending Speed Peak Amplitude (RPM) | Sampling Time Point (sec) | API 1 BU % RSD |
|---|---|---|---|---|---|---|---|---|---|---|---|---|
|  |  | X10 | X50 | X90 | X10 | X50 | X90 |  |  |  |  |  |
| 15 | 3 | 0.7 | 1.6 | 3.4 | 0.8 | 2.0 | 4.2 | 24 | 100 | 1780 | 60 | 5.3 |
|  |  |  |  |  |  |  |  |  |  |  | 120 | 1.1 |
|  |  |  |  |  |  |  |  |  |  |  | 180 | 1.0 |
|  |  |  |  |  |  |  |  |  |  |  | 240 | 1.5 |
|  |  |  |  |  |  |  |  |  |  |  | 300 | 1.0 |
|  |  |  |  |  |  |  |  |  |  |  | 360 | 1.9 |
| 16 | 3 | 0.7 | 1.6 | 3.4 | 0.8 | 2.0 | 4.2 | 50 | 200 | 1780 | 10 | 10.7 |
|  |  |  |  |  |  |  |  |  |  |  | 20 | 3.9 |
|  |  |  |  |  |  |  |  |  |  |  | 30 | 8.9 |
|  |  |  |  |  |  |  |  |  |  |  | 45 | 11.4 |
|  |  |  |  |  |  |  |  |  |  |  | 60 | 12.1 |
|  |  |  |  |  |  |  |  |  |  |  | 90 | 4.1 |
|  |  |  |  |  |  |  |  |  |  |  | 120 | 3.3 |
|  |  |  |  |  |  |  |  |  |  |  | 180 | 3.1 |
| 17 | 3 | 0.7 | 1.6 | 3.4 | 0.8 | 2.0 | 4.2 | 72 | 300 | 1780 | 60 | 2.5 |
|  |  |  |  |  |  |  |  |  |  |  | 120 | 19.9 |
|  |  |  |  |  |  |  |  |  |  |  | 180 | 1.9 |
|  |  |  |  |  |  |  |  |  |  |  | 240 | 2.7 |
|  |  |  |  |  |  |  |  |  |  |  | 300 | 0.6 |
|  |  |  |  |  |  |  |  |  |  |  | 360 | 26.7 |
|  |  |  |  |  |  |  |  |  |  |  | 420 | 57.3 |

| Embodiment | API 2 BU % RSD | API 1/API 2 % of Theoretical | API 1 Assay % of Theoretical | API 2 Assay % of Theoretical | Acceleration Pulse (sec) | Deceleration Pulse (sec) | Total # of Pulse Cycles |
|---|---|---|---|---|---|---|---|
| 15 | 4.5 | 102 | 104 | 102 | 30 | 30 | 2 |
|  | 1.0 | 100 | 98 | 98 | 30 | 30 | 4 |
|  | 1.0 | 100 | 97 | 98 | 30 | 30 | 6 |

TABLE 5-continued

Ternary blends of API 1 (Fluticasone Propionate), API 2(Salmeterol Xinafoate) and coarse carrier (Lactose LH 200) using Blender 1 at 0.7 L vessel volume with the 'Pulsating' blending process.

|    |      |     |     |     |    |    |    |
|----|------|-----|-----|-----|----|----|----|
|    | 1.7  | 101 | 98  | 97  | 30 | 30 | 8  |
|    | 1.2  | 101 | 97  | 97  | 30 | 30 | 10 |
|    | 1.8  | 100 | 96  | 96  | 30 | 30 | 12 |
| 16 | 34.4 | 96  | 94  | 105 | 10 | 10 | 2  |
|    | 5.6  | 100 | 100 | 100 | 10 | 10 | 4  |
|    | 9.2  | 100 | 102 | 102 | 10 | 10 | 6  |
|    | 9.4  | 98  | 93  | 94  | 15 | 10 | 8  |
|    | 12.1 | 98  | 88  | 89  | 15 | 10 | 10 |
|    | 3.9  | 99  | 92  | 92  | 30 | 10 | 11 |
|    | 3.3  | 100 | 95  | 95  | 30 | 30 | 12 |
|    | 2.9  | 100 | 96  | 96  | 30 | 30 | 14 |
| 17 | 2.2  | 100 | 102 | 101 | 30 | 30 | 2  |
|    | 19.9 | 101 | 106 | 105 | 30 | 30 | 4  |
|    | 1.7  | 101 | 97  | 96  | 30 | 30 | 6  |
|    | 2.7  | 101 | 96  | 95  | 30 | 30 | 8  |
|    | 0.9  | 100 | 94  | 94  | 30 | 30 | 10 |
|    | 26.7 | 101 | 103 | 102 | 30 | 30 | 12 |
|    | 61.1 | 101 | 102 | 103 | 30 | 30 | 14 |

TABLE 6

Ternary blends of API 1 (Fluticasone Propionate), API 2(Salmeterol Xinafoate) and coarse carrier (Lactose LH 200) using Blender 2 at 1.0 L and 2.0 L vessel volume with the 'Pulsating' blending process.

| Embodiment | Blend Strength | Vessel Size (L) | API 1 PPS (µm) | | | API 2 PPS (µm) | | | Vessel Loading (%) | Batch Size (grams) | Blending Speed Peak Amplitude (RPM) | Sampling Time Point (sec) |
|---|---|---|---|---|---|---|---|---|---|---|---|---|
| | | | X10 | X50 | X90 | X10 | X50 | X90 | | | | |
| 18 | 3 | 1.0 | 0.7 | 1.6 | 3.4 | 0.9 | 2.3 | 4.7 | 50 | 300 | 1500 | 60 |
| | | | | | | | | | | | | 120 |
| | | | | | | | | | | | | 180 |
| 19 | 3 | 1.0 | 0.7 | 1.6 | 3.4 | 0.8 | 2.0 | 4.2 | 50 | 300 | 1500 | 60 |
| | | | | | | | | | | | | 120 |
| | | | | | | | | | | | | 180 |
| 20 | 3 | 2.0 | 0.7 | 1.6 | 3.4 | 0.8 | 2.0 | 4.2 | 50 | 600 | 1500 | 60 |
| | | | | | | | | | | | | 120 |
| | | | | | | | | | | | | 180 |

| Embodiment | API 1 BU % RSD | API 2 BU % RSD | API 1/API 2 % of Theoretical | API 1 Assay % of Theoretical | API 2 Assay % of Theoretical | Acceleration Pulse (sec) | Deceleration Pulse (sec) | Total # of Pulse Cycles |
|---|---|---|---|---|---|---|---|---|
| 18 | 2.6 | 3.2 | 98 | 96 | 98 | 30 | 30 | 2 |
|    | 0.8 | 1.9 | 98 | 96 | 97 | 30 | 30 | 4 |
|    | 1.4 | 1.8 | 98 | 96 | 98 | 30 | 30 | 6 |
| 19 | 6.0 | 6.6 | 97 | 101 | 104 | 30 | 30 | 2 |
|    | 1.9 | 3.6 | 95 | 98 | 103 | 30 | 30 | 4 |
|    | 3.0 | 3.9 | 96 | 100 | 104 | 30 | 30 | 6 |
| 20 | 1.8 | 1.6 | 101 | 99 | 98 | 30 | 30 | 2 |
|    | 2.8 | 2.6 | 101 | 98 | 98 | 30 | 30 | 4 |
|    | 2.4 | 2.6 | 100 | 98 | 98 | 30 | 30 | 6 |

TABLE 7

Ternary blends of API 1 (Fluticasone Propionate), API 2(Salmeterol Xinafoate) and coarse carrier (Lactose LH 200) using Blender 2 at 2.0 L vessel volume.

| Embodiment | Blend Strength | API 1 PPS (µm) | | | API 2 PPS (µm) | | | Vessel Loading (%) | Batch Size (grams) | Blending Speed Peak Amplitude (RPM) | Sampling Time Point (sec) | API 1 BU % RSD |
|---|---|---|---|---|---|---|---|---|---|---|---|---|
| | | X10 | X50 | X90 | X10 | X50 | X90 | | | | | |
| 21 | 3 | 0.7 | 1.6 | 3.4 | 0.8 | 2.0 | 4.2 | 50 | 600 | 1500 | 10 | 4.1 |
| | | | | | | | | | | | 20 | 2.1 |
| | | | | | | | | | | | 30 | 0.9 |
| | | | | | | | | | | | 60 | 2.1 |

TABLE 7-continued

Ternary blends of API 1 (Fluticasone Propionate), API 2(Salmeterol Xinafoate) and coarse carrier (Lactose LH 200) using Blender 2 at 2.0 L vessel volume.

|    |   |     |     |     |     |     |     |    |     |      |     |     |
|----|---|-----|-----|-----|-----|-----|-----|----|-----|------|-----|-----|
|    |   |     |     |     |     |     |     |    |     |      | 90  | 1.7 |
|    |   |     |     |     |     |     |     |    |     |      | 120 | 1.7 |
|    |   |     |     |     |     |     |     |    |     |      | 180 | 3.2 |
| 22 | 3 | 0.7 | 1.6 | 3.4 | 0.8 | 2.0 | 4.2 | 50 | 600 | 1000 | 10  | 1.3 |
|    |   |     |     |     |     |     |     |    |     |      | 20  | 2.4 |
|    |   |     |     |     |     |     |     |    |     |      | 30  | 1.0 |
|    |   |     |     |     |     |     |     |    |     |      | 45  | 1.6 |
|    |   |     |     |     |     |     |     |    |     |      | 60  | 1.5 |
|    |   |     |     |     |     |     |     |    |     |      | 90  | 2.0 |
|    |   |     |     |     |     |     |     |    |     |      | 120 | 2.7 |
|    |   |     |     |     |     |     |     |    |     |      | 180 | 1.6 |
| 23 | 3 | 0.7 | 1.6 | 3.4 | 0.8 | 2.0 | 4.2 | 50 | 600 | 500  | 10  | 5.1 |
|    |   |     |     |     |     |     |     |    |     |      | 20  | 2.3 |
|    |   |     |     |     |     |     |     |    |     |      | 30  | 7.1 |
|    |   |     |     |     |     |     |     |    |     |      | 45  | 2.9 |
|    |   |     |     |     |     |     |     |    |     |      | 60  | 6.5 |
|    |   |     |     |     |     |     |     |    |     |      | 90  | 3.4 |
|    |   |     |     |     |     |     |     |    |     |      | 120 | 1.8 |
|    |   |     |     |     |     |     |     |    |     |      | 150 | 2.7 |
|    |   |     |     |     |     |     |     |    |     |      | 180 | 7.4 |
|    |   |     |     |     |     |     |     |    |     |      | 240 | 2.9 |

| Embodiment | API 2 BU % RSD | API 1/API 2 % of Theoretical | API 1 Assay % of Theoretical | API 2 Assay % of Theoretical | Acceleration Pulse (sec) | Deceleration Pulse (sec) | Total # of Pulse Cycles |
|---|---|---|---|---|---|---|---|
| 21 | 3.3 | 97 | 106 | 109 | 10 | 10 | 2 |
|    | 1.7 | 97 | 103 | 106 | 10 | 10 | 4 |
|    | 1.8 | 97 | 103 | 107 | 10 | 10 | 6 |
|    | 2.1 | 97 | 103 | 106 | 30 | 30 | 8 |
|    | 2.4 | 96 | 101 | 105 | 30 | 30 | 10 |
|    | 1.4 | 98 | 101 | 103 | 30 | 30 | 12 |
|    | 3.0 | 96 | 103 | 107 | 30 | 30 | 16 |
| 22 | 5.2 | 94 | 101 | 108 | 10 | 10 | 2 |
|    | 3.5 | 97 | 102 | 106 | 10 | 10 | 4 |
|    | 4.2 | 96 | 102 | 107 | 10 | 10 | 6 |
|    | 2.0 | 97 | 101 | 105 | 15 | 15 | 8 |
|    | 2.1 | 97 | 101 | 105 | 15 | 15 | 10 |
|    | 1.5 | 98 | 100 | 101 | 30 | 30 | 1 |
|    | 3.4 | 97 | 102 | 104 | 30 | 30 | 1 |
|    | 1.4 | 98 | 99 | 101 | 30 | 30 | 2 |
| 23 | 14.6 | 100 | 99 | 101 | 10 | 10 | 2 |
|    | 8.8 | 96 | 99 | 105 | 10 | 10 | 4 |
|    | 8.8 | 102 | 103 | 102 | 10 | 10 | 6 |
|    | 6.9 | 97 | 104 | 108 | 15 | 15 | 8 |
|    | 4.9 | 103 | 108 | 106 | 15 | 15 | 10 |
|    | 5.6 | 100 | 109 | 110 | 30 | 30 | 11 |
|    | 5.6 | 99 | 106 | 108 | 30 | 30 | 12 |
|    | 2.7 | 100 | 105 | 106 | 30 | 30 | 13 |
|    | 4.3 | 102 | 110 | 107 | 30 | 30 | 14 |
|    | 2.4 | 101 | 107 | 105 | 30 | 30 | 16 |

TABLE 8

Binary and Ternary blends of API 1 (Fluticasone Propionate), API 2 (Salmeterol Xinafoate) and coarse carrier (Lactose LH 200) using Blender 3 at 5.0 L vessel volume with the 'Pulsating' blending process.

| Embodiment | Strength | API 1 PPS (µm) | | | API 2 PPS (µm) | | | Vessel Loading (%) | Batch Size (grams) | Blending Speed Peak Amplitude (RPM) | Sampling Time Point (sec) | API 1 BU % RSD |
|---|---|---|---|---|---|---|---|---|---|---|---|---|
|   |   | X10 | X50 | X90 | X10 | X50 | X90 |   |   |   |   |   |
| 24 | 6 | 1.0 | 2.2 | 4.2 | N/A | N/A | N/A | 50 | 1475 | 1100 | 10 | 15.2 |
|    |   |     |     |     |     |     |     |    |      |      | 20 | 2.6 |
|    |   |     |     |     |     |     |     |    |      |      | 30 | 1.7 |
|    |   |     |     |     |     |     |     |    |      |      | 45 | 2.7 |
|    |   |     |     |     |     |     |     |    |      |      | 60 | 2.1 |
|    |   |     |     |     |     |     |     |    |      |      | 90 | 2.0 |
|    |   |     |     |     |     |     |     |    |      |      | 120 | 1.9 |
|    |   |     |     |     |     |     |     |    |      |      | 180 | 1.8 |

TABLE 8-continued

Binary and Ternary blends of API 1 (Fluticasone Propionate), API 2 (Salmeterol Xinafoate) and coarse carrier (Lactose LH 200) using Blender 3 at 5.0 L vessel volume with the 'Pulsating' blending process.

| Embodiment | Strength | API 1 PPS (μm) X10 | X50 | X90 | API 2 PPS (μm) X10 | X50 | X90 | Vessel Loading (%) | Batch Size (grams) | Blending Speed Peak Amplitude (RPM) | Sampling Time Point (sec) | API 1 BU % RSD |
|---|---|---|---|---|---|---|---|---|---|---|---|---|
| | | | | | | | | | | | 240 | 2.5 |
| | | | | | | | | | | | 300 | 1.6 |
| 25 | 3 | N/A | N/A | N/A | 1.1 | 2.5 | 4.9 | 50 | 1475 | 1979 | 20 | N/A |
| | | | | | | | | | | | 30 | N/A |
| | | | | | | | | | | | 45 | N/A |
| | | | | | | | | | | | 65 | N/A |
| | | | | | | | | | | | 90 | N/A |
| | | | | | | | | | | | 120 | N/A |
| | | | | | | | | | | | 180 | N/A |
| 26 | 3 | 0.7 | 1.6 | 3.4 | 1.0 | 2.1 | 4.2 | 56 | 1670 | 800 | 360 | 1.2 |
| 27 | 3 | 1.0 | 2.2 | 4.2 | 1.1 | 2.5 | 4.9 | 50 | 1475 | 1306 | 30 | 7.8 |
| | | | | | | | | | | | 60 | 2.8 |
| | | | | | | | | | | | 90 | 2.9 |
| | | | | | | | | | | | 120 | 1.8 |
| | | | | | | | | | | | 180 | 1.9 |
| 28 | 3 | 0.8 | 1.6 | 3.2 | 1.1 | 2.5 | 4.7 | 56 | 1670 | 1500 | 120 | 1.3 |
| | | | | | | | | | | | 180 | 1.8 |

| Embodiment | API 2 BU % RSD | API 1/API 2 % of Theoretical | API 1 Assay % of Theoretical | API 2 Assay % of Theoretical | Acceleration Pulse (sec) | Deceleration Pulse (sec) | Total # of Pulse Cycles |
|---|---|---|---|---|---|---|---|
| 24 | N/A | N/A | 104 | N/A | 10 | 10 | 2 |
| | N/A | N/A | 100 | N/A | 10 | 10 | 4 |
| | N/A | N/A | 99 | N/A | 10 | 10 | 6 |
| | N/A | N/A | 100 | N/A | 15 | 15 | 8 |
| | N/A | N/A | 99 | N/A | 15 | 15 | 10 |
| | N/A | N/A | 101 | N/A | 30 | 30 | 12 |
| | N/A | N/A | 100 | N/A | 30 | 30 | 14 |
| | N/A | N/A | 99 | N/A | 60 | 60 | 16 |
| | N/A | N/A | 99 | N/A | 60 | 60 | 18 |
| | N/A | N/A | 99 | N/A | 60 | 60 | 20 |
| 25 | 4.3 | N/A | N/A | 103 | 20 | 20 | 2 |
| | 1.5 | N/A | N/A | 101 | 10 | 10 | 4 |
| | 2.2 | N/A | N/A | 100 | 15 | 15 | 6 |
| | 1.4 | N/A | N/A | 99 | 20 | 20 | 8 |
| | 2.2 | N/A | N/A | 99 | 25 | 25 | 10 |
| | 3.7 | N/A | N/A | 100 | 30 | 30 | 12 |
| | 1.8 | N/A | N/A | 96 | 60 | 60 | 14 |
| 26 | 1.6 | 0.9 | 98 | 96 | 60 | 60 | 12 |
| 27 | 6.9 | 1.4 | 100 | 98 | 30 | 30 | 2 |
| | 2.1 | 3.5 | 104 | 100 | 30 | 30 | 4 |
| | 3.3 | 0.7 | 101 | 99 | 30 | 30 | 6 |
| | 1.8 | 0.4 | 101 | 99 | 30 | 30 | 8 |
| | 1.7 | 0.8 | 101 | 99 | 60 | 60 | 10 |
| 28 | 3.0 | 1.9 | 99 | 99 | 60 | 60 | 4 |
| | 2.0 | 0.4 | 99 | 98 | 60 | 60 | 6 |

TABLE 9

Ternary blends of API 1 (Fluticasone Propionate), API 2 (Salmeterol Xinafoate) and coarse carrier (Lactose LH 200) using Blender 3 at 30.0 L vessel volume with the 'Pulsating' blending process.

| Embodiment | Strength | API 1 PPS (μm) X10 | X50 | X90 | API 2 PPS (μm) X10 | X50 | X90 | Vessel Loading (%) | Batch Size (grams) | Blending Speed Peak Amplitude (RPM) | Sampling Time Point (sec) | API 1 BU % RSD |
|---|---|---|---|---|---|---|---|---|---|---|---|---|
| 29 | 3 | 0.8 | 2.0 | 5.1 | 0.9 | 1.8 | 3.5 | 40 | 7250 | 860 | 240 | 1.2 |
| 30 | 3 | 0.9 | 2.1 | 4.1 | 1.0 | 2.3 | 4.8 | 56 | 10000 | 700 | 60 | 5.5 |
| | | | | | | | | | | | 120 | 4.5 |
| | | | | | | | | | | | 180 | 4.8 |
| | | | | | | | | | | | 240 | 1.5 |
| 31 | 3 | 0.9 | 2.1 | 4.1 | 1.0 | 2.3 | 4.8 | 56 | 10000 | 860 | 60 | 2.1 |
| | | | | | | | | | | | 120 | 1.6 |
| | | | | | | | | | | | 180 | 3.2 |
| | | | | | | | | | | | 240 | 1.2 |
| 32 | 3 | 0.7 | 1.9 | 3.2 | 0.9 | 1.8 | 3.5 | 56 | 10000 | 860 | 120 | 5.8 |
| | | | | | | | | | | | 240 | 1.1 |

TABLE 9-continued

Ternary blends of API 1 (Fluticasone Propionate), API 2 (Salmeterol Xinafoate) and coarse carrier (Lactose LH 200) using Blender 3 at 30.0 L vessel volume with the 'Pulsating' blending process.

| Embodiment | API 2 BU % RSD | API 1/API 2 % of Theoretical | API 1 Assay % of Theoretical | API 2 Assay % of Theoretical | Acceleration Pulse (sec) | Deceleration Pulse (sec) | Total # of Pulse Cycles |
|---|---|---|---|---|---|---|---|
| 29 | 2.5 | 2.4 | 101 | 103 | 60 | 60 | 8 |
| 30 | 1.6 | 5.6 | 95 | 99 | 60 | 60 | 2 |
|  | 2.3 | 5.6 | 96 | 100 | 60 | 60 | 4 |
|  | 1.6 | 4.4 | 101 | 100 | 60 | 60 | 6 |
|  | 1.6 | 0.4 | 98 | 99 | 66 | 60 | 8 |
| 31 | 1.4 | 2.4 | 100 | 102 | 60 | 60 | 2 |
|  | 1.7 | 2.0 | 100 | 101 | 60 | 60 | 4 |
|  | 3.2 | 0.5 | 99 | 101 | 60 | 60 | 6 |
|  | 1.2 | 0.4 | 99 | 100 | 66 | 60 | 8 |
| 32 | 5.4 | 2.0 | 111 | 106 | 60 | 60 | 4 |
|  | 1.2 | 0.6 | 106 | 105 | 60 | 60 | 8 |

The invention claimed is:

1. A single step process of producing a dry microparticulate powder blend comprising pulsating blending of one or more micronized active pharmaceutical ingredient(s) and one or more pharmaceutically acceptable micronized excipient(s), wherein the process is completed within 4 minutes.

2. The process according to claim 1 wherein the micronized active pharmaceutical ingredient has a mass median particle size of about 0.1 µm to about 20 µm.

3. The process according to claim 1 wherein the micronized active pharmaceutical ingredient has a mass median particle size of about 1 µm to about 5 µm.

4. The process according to claim 1 wherein the active pharmaceutical ingredient is selected from the group consisting of non-steroidal anti-inflammatory agents, corticosteroids, anti-neoplastic, anti-microbial agents, anti-viral, anti-bacterial agents, anti-fungal, anti-asthmatics, bronchodilators, antihistamines, muscarinic antagonist, immunosuppressive agents, anti-anxiety agents, sedatives/hypnotics, anti-psychotic agents, anticonvulsants, and calcium channel blockers.

5. The process according to claim 1 wherein the pharmaceutically acceptable micronized excipient has a mass median particle size of about 1 µm to about 20 µm.

6. The process according to claim 1 wherein the pharmaceutically acceptable micronized excipient is selected from the group consisting of lactose, glucose, fructose, sucrose, raffinose, mannose, dextrose, trehalose, trileucine, leucine, methionine, mannitol, maltitol, xylitol, glycine, sorbitol, erythritol, phosphatidylcholines (e.g, DSPC, DSPE etc.), starches, carbohydrates, cyclodextrin, calcium salts (e.g., calcium chloride, calcium sulfate), iron salts, cellulose and derivatives thereof.

7. The process according to claim 1 wherein the pharmaceutically acceptable micronized excipient is lactose.

8. The process according to claim 1 wherein the active pharmaceutical ingredient(s) and pharmaceutically acceptable micronized excipient(s) are sieved.

9. A single step process of producing a dry microparticulate powder blend comprising pulsating blending of one or more micronized active pharmaceutical ingredient(s) and one or more pharmaceutically acceptable carrier(s), wherein the process is completed within 4 minutes.

10. The process according to claim 9 wherein, the pharmaceutically acceptable carrier is micronized.

11. The process according to claim 9 wherein the micronized active pharmaceutical ingredient has a mass median particle size of about 0.1 µm to about 20 µm.

12. The process according to claim 9 wherein the micronized active pharmaceutical ingredient has a mass median particle size of about 1 µm to about 5 µm.

13. The process according to claim 9 wherein the active pharmaceutical ingredient is selected from the group consisting of non-steroidal anti-inflammatory agents, corticosteroids, anti-neoplastic, anti-microbial agents, anti-viral, anti-bacterial agents, anti-fungal, anti-asthmatics, bronchodilators, antihistamines, muscarinic antagonist, immunosuppressive agents, anti-anxiety agents, sedatives/hypnotics, anti-psychotic agents, anticonvulsants and calcium channel blockers.

14. The process according to claim 9 wherein the pharmaceutically acceptable carrier has a mass median particle size of about 1 µm to 1000 µm.

15. The process according to claim 9 wherein the pharmaceutically acceptable carrier is selected from the group consisting of lactose, glucose, fructose, sucrose, raffinose, mannose, dextrose, trehalose, trileucine, leucine, mannitol, maltitol, xylitol, glycine, sorbitol, erythritol, phosphatidylcholines (e.g. DSPC, DSPE etc.), calcium salts (e.g., calcium chloride, calcium sulfate), iron salts, starches, carbohydrates, cyclodextrin, cellulose and derivatives thereof.

16. The process according to claim 9 wherein the pharmaceutically acceptable carrier is lactose.

17. The process according to claim 9 wherein the pharmaceutically acceptable carrier is lactose and has a mass median particle size of about 50 µm to about 100 µm.

18. The process according to claim 9 wherein the active pharmaceutical ingredient(s) and pharmaceutically acceptable carrier(s) are sieved.

19. A single step process of producing a dry microparticulate powder blend comprising pulsating blending of one or more micronized active pharmaceutical ingredient(s), one or more micronized pharmaceutically acceptable excipient(s) and one or more pharmaceutically acceptable carrier(s), wherein the process is completed within 4 minutes.

20. The process according to claim 19 wherein the pharmaceutically acceptable carrier is micronized.

21. The process according to claim 19 wherein the micronized active pharmaceutical ingredient has a mass median particle size of about 0.1 µm to about 20 µm.

22. The process according to claim 19 wherein the micronized active pharmaceutical ingredient has a mass median particle size of about 1 µm to about 5 µm.

23. The process according to claim 19 wherein the active pharmaceutical ingredient is selected from the group consisting of non-steroidal anti-inflammatory agents, corticosteroids, anti-neoplastic, anti-microbial agents, anti-viral, anti-bacterial agents, anti-fungal, anti-asthmatics, bronchodilators, antihistamines, muscarinic antagonist, immunosuppressive agents, anti-anxiety agents, sedatives/hypnotics, anti-psychotic agents, anticonvulsants, and calcium channel blockers.

24. The process according to claim 19 wherein the pharmaceutically acceptable carrier has a mass median particle size of about 1 μm to about 1000 μm.

25. The process according to claim 19 wherein the pharmaceutically acceptable carrier is selected from the group consisting of lactose, glucose, fructose, sucrose, raffinose, mannose, dextrose, trehalose, trileucine, leucine, mannitol, maltitol, xylitol, glycine, sorbitol, erythritol, phosphatidylcholines (e.g. DSPC, DSPE etc.), calcium salts (e.g., calcium chloride, calcium sulfate), iron salts, starches, carbohydrates, cyclodextrin, cellulose and derivatives thereof.

26. The process according to claim 19 wherein the pharmaceutically acceptable carrier is lactose.

27. The process according to claim 19 wherein the pharmaceutically acceptable carrier is lactose and has a mass median particle size of about 50 μm to about 100 μm.

28. The process according to claim 19 wherein the pharmaceutically acceptable micronized excipient has a mass median particle size of about 20 μm or less.

29. The process according to claims 19 wherein the pharmaceutically acceptable micronized excipient is selected from the group consisting of lactose, glucose, fructose, sucrose, raffinose, mannose, dextrose, trehalose, trileucine, leucine, methionine, mannitol, maltitol, xylitol, glycine, sorbitol, erythritol, phosphatidylcholines (e.g. DSPC, DSPE etc.), starches, carbohydrates, cyclodextrin, calcium salts (e.g., calcium chloride, calcium sulfate), iron salts, cellulose and derivatives thereof.

30. The process according to claim 19 wherein the pharmaceutically acceptable micronized excipient is lactose.

31. The process according to claim 19 wherein the active pharmaceutical ingredient(s), pharmaceutically acceptable carrier(s) and pharmaceutically acceptable micronized excipient(s) are sieved.

* * * * *